(12) United States Patent
Phifer (10) Patent No.: US 6,409,970 B1
(45) Date of Patent: Jun. 25, 2002

(54) BIOPSY COLLECTION SYSTEM (76) Inventor: Christopher R. Phifer, 1460 Allentown Rd., Lansdale, PA (US) 19446

( * ) Notice: Subject to any disclaimer, the term of this patent is extended or adjusted under 35 U.S.C. 154(b) by 0 days.

(21) Appl. No.: 09/739,434

(22) Filed: Dec. 18, 2000

(51) Int. Cl.⁷ .................................................. G01N 1/28
(52) U.S. Cl. ..................... 422/102; 422/104; 356/239.6; 356/237.6; 362/97
(58) Field of Search .......................... 422/82.05, 82.09, 422/99, 102, 104; 356/58–61, 64–67, 239.6, 237.6; 362/97

(56) References Cited

U.S. PATENT DOCUMENTS

| 1,209,651 | A | * | 12/1916 | Mignone | |
| 2,368,350 | A | * | 1/1945 | Ellison | |
| 3,767,303 | A | * | 10/1973 | Foufounis et al. | 356/63 |
| 3,969,227 | A | * | 7/1976 | Garris | 209/73 |
| 4,071,883 | A | | 1/1978 | Dennis | 362/97 |
| 4,185,407 | A | | 1/1980 | Lamb | 40/367 |
| 4,647,162 | A | * | 3/1987 | Godard et al. | 350/574 |
| 4,764,342 | A | * | 8/1988 | Kelln et al. | 422/72 |
| 4,936,682 | A | * | 6/1990 | Hoyt | 356/414 |
| 5,518,923 | A | * | 5/1996 | Berndt et al. | 435/287.3 |
| 5,605,393 | A | | 2/1997 | Cucchi et al. | 362/97 |
| 5,816,171 | A | | 10/1998 | Fitts, Jr. | 108/23 |

* cited by examiner

Primary Examiner—Jeffrey Snay

(57) ABSTRACT

A biopsy collection system for use during colonoscopies, esophagogastroduodenoscopy, prostate and liver procedures. The system provides a device and method which enable safe and secure handling of transparent specimen containers during a biopsy collection procedure and which permit the ready visualization of minuscule tissue samples within a minimum of time during such a procedure. The device includes structure for safely securing transparent specimen containers in a hands-free condition on the device and structure for selectively illuminating one or more of the specimen containers by a light source directing light upwardly through the specimen container so that a person looking from a position above the specimen container can readily visualize the presence and quality of a minuscule tissue sample.

14 Claims, 10 Drawing Sheets

BIOPSY COLLECTION SYSTEM

FIELD OF THE INVENTION

The present invention relates generally to the field of medical procedures in which pathology specimens are obtained by biopsy, and more particularly, the present invention relates to a device and method which enable ready handling, securement, visualization, and identification of minuscule tissue samples obtained during medical procedures.

BACKGROUND OF THE INVENTION

Significant advancements have been made in research and development in the medical industry in the area of diagnostic procedures. The use of biopsies for pathology review has become the single most effective manner for physicians to definitely diagnose disease and the state of illness. The use of endoscopic examinations in the specialties of gastroenterology, urology, otolaryngology, and pulmonology has specifically increased in popularity. The effective use of such examinations can be seen, for instance, from the fact that colon and prostate cancer have recently shown a downward trend believed partly to be a result of the use of endoscopic exams utilizing biopsies as an early diagnostic tool.

A typical procedure for collecting biopsies involves taking minuscule tissue samples from a patient and placing the samples in a clear liquid in various sized transparent specimen containers. The specimen containers are then forwarded to a pathology department for various diagnostic testing of the contained specimens.

Various problems relating to the handling of biopsy specimens can arise during biopsy collection procedures typically because the biopsy specimens are minuscule in size and are difficult to visualize. For example, a mishandling problem may result from unknown spillage of the specimen and/or the inability to quickly and positively visualize and confirm the presence of a desired specimen within the specimen container. Such problems may require a biopsy collection procedure to be unduly lengthened or repeated. This, in turn, increases the potential for complications and causes patient discomfort.

The quality of the specimen taken and the ability to confirm the quality of the specimen provides another important consideration. The size and depth of a biopsy is an important factor when pathological determination is required for a differential diagnosis. It is not uncommon that biopsies of insufficient quality are returned as an inadequate specimen or that the desired specimen is not found by the pathology department.

Insufficient lighting often exaggerates the problem of visualizing a minuscule tissue sample. Although the use of specialized lighting devices, such as light boxes and the like, are not believed to be utilized during biopsy specimen collection procedures, the use of light boxes in unrelated arts is disclosed, for instance, by U.S. Pat. No. 4,071,883 issued to Dennis; U.S. Pat. No. 5,605,393 issued to Cucchi et al.; U.S. Pat. No. 4,185,407 issued to Lamb; and U.S. Pat. No. 5,816,171 issued to Fitts. The Dennis patent discloses the use of a light box for observation and photographic procedures performed in virological, microbiological and clinical laboratories. The Cucchi patent discloses the use of a table which has a light emitting plane and which is used for the treatment of animals. In the embodiment illustrated in FIGS. 5 and 6 of the Lamb patent, an illuminated display device is disclosed having an upper wall which is rotatable relative to a bottom wall of the device. The Fitts patent discloses a rotating illuminating table.

Although the above referenced biopsy collection procedures and the non-related use of light boxes disclosed in the above referenced patents may be satisfactory for their intended purposes, there is a need for a specialized device and method enabling ready handling, securement, visualization, and identification of minuscule tissue samples obtained during a medical procedure. The device and method should aid a physician, nurse and/or technician in efficiently collecting and forwarding desired specimens to a pathology lab and should significantly reduce, if not eliminate, the occurrence of lost, spilled, misplaced and/or mislabeled specimens regardless of the size of the specimens or of the lighting conditions in the area in which the biopsy collection procedure is performed. In addition, the device and method should permit minuscule specimens to be readily visualized so that the user can readily confirm the presence and determine the quality of the specimen.

OBJECTS OF THE INVENTION

With the foregoing in mind, a primary object of the present invention is to provide a device and method for use in properly visualizing and collecting biopsy specimens.

Another object of the present invention is to provide a device to which specimen containers can be safely secured to prevent spillage of the specimen and to free the hands of the physician, nurse, and/or technician.

Still another object of the present invention is to provide a visualization, securement, identification and handling aid to meet the physician's, nurse's and/or technician's need for efficiently performing his/her duty during a biopsy collection procedure.

A further object of the present invention is to provide a physician, nurse, and/or technician with the ability to accurately and clearly view a biopsy which, in turn, results in a reduction in time required to confirm the presence of a desired specimen, a reduction in the speculations as to the quality of the biopsy, and a reduction of the likelihood of having to repeat the biopsy collection procedure for reasons of insufficient specimen.

SUMMARY OF THE INVENTION

More specifically, according to one aspect of the present invention, a biopsy collection device is provided for use in safely securing and positively visualizing a biopsy specimen located in a specimen container. The device includes a base unit and an overlying carrousel, or turntable, which is mounted on the base unit such that it is rotatable relative to the base unit. The base unit houses a light source directing light toward the carrousel, and the carrousel has a plurality of securement means for positively and safely securing specimen containers to the carrousel. Thus, as the carrousel is rotated relative to the base unit, it positions at least a selected one of the specimen containers in a position for illumination by the light source thereby aiding the visualization of a biopsy specimen located in the specimen container. Preferably, the securement means is a plurality of spaced-apart, upwardly-opening recesses which are formed in the carrousel and which each hold a single specimen container. In addition, preferably the carrousel includes a graphic overlay or like indicia which positively identifies each recess with a corresponding predetermined biopsy specimen.

According to another aspect of the present invention, a novel method is provided for collecting biopsy specimens.

The method includes the steps of placing biopsy specimens in specimen containers and securing the specimen containers on a carrousel, or turntable, mounted on a base unit having a light source directing light upwardly into at least a selected one of the specimen containers. In addition, the method includes visualizing each biopsy specimen by rotating the turntable relative to the base unit so that each specimen container, preferably one-by-one, is illuminated by the light source. Furthermore, the method includes the step of positively identifying each biopsy specimen by locating the specimen containers on the turntable in locations specifically designated for predetermined biopsy specimen types.

BRIEF DESCRIPTION OF THE DRAWINGS

The foregoing and other objects, features and advantages of the present invention should become apparent from the following description when taken in conjunction with the accompanying drawings, in which.

DETAILED DESCRIPTION OF THE PREFERRED EMBODIMENT

The present invention relates to the structure and use of a biopsy collection device which enables safe and secure handling of transparent specimen containers during a biopsy collection procedure and which permits the ready visualization of minuscule tissue samples within a minimum of time during such a procedure. Thus, a device according to the present invention includes means for safely securing transparent specimen containers in a hands-free condition on the device and means for selectively illuminating one or more of the specimen containers by a light source directing light upwardly through the specimen container so that a person looking from a position above the specimen container can readily visualize the presence and quality of a minuscule tissue sample.

Figure 1:
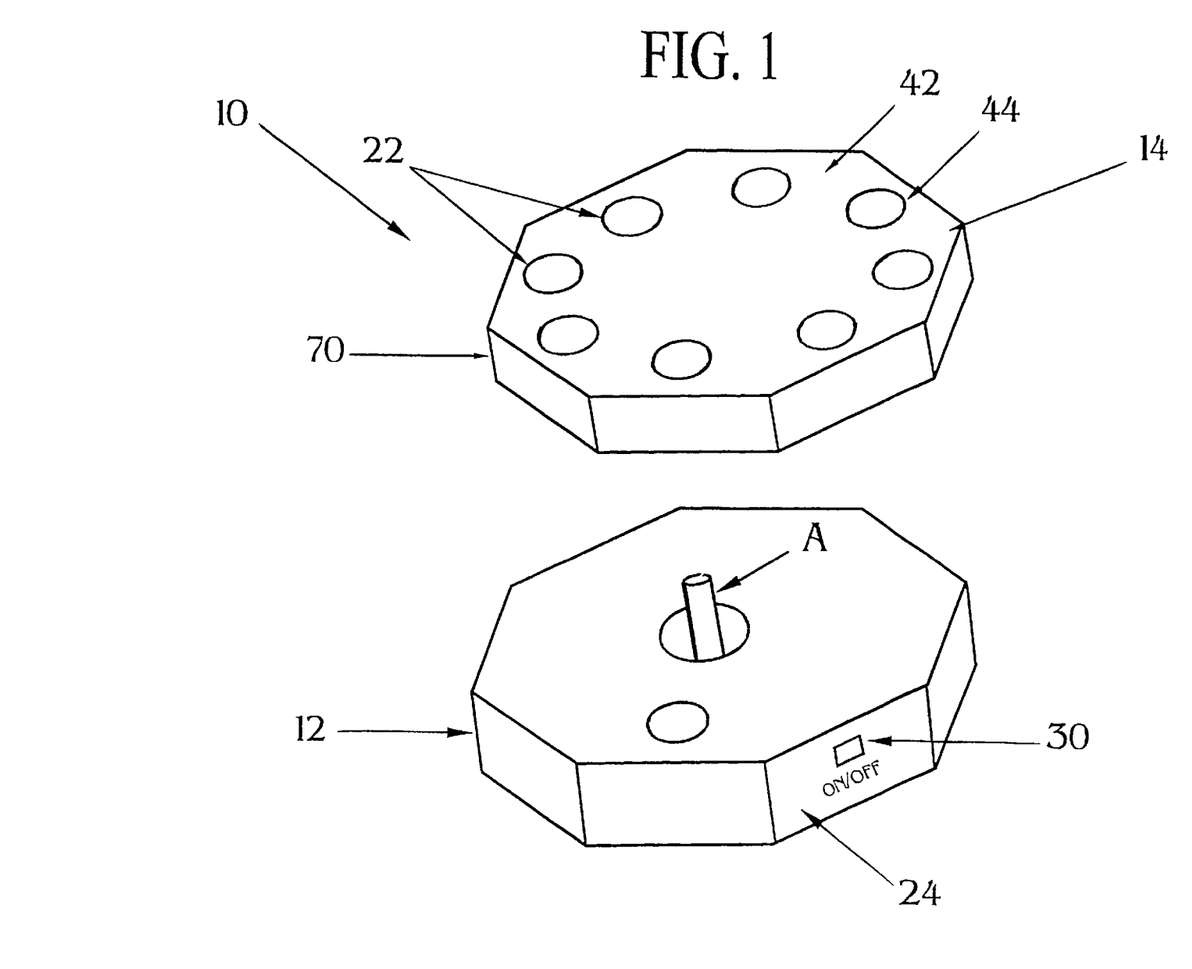
FIG. 1 is an exploded perspective view of a biopsy collection device according to the present invention.

As illustrated in FIG. 1, a preferred biopsy collection device 10 according to the present invention includes a base unit 12 and a carrousel, or turntable, 14 mounted for rotation thereon about a central vertical axis of rotation "A". The base unit 12 houses a light source 16 directing light upwardly through a window 18 formed in an upper surface 20 of the base unit 12. The carrousel 14 has means 22 for securing transparent specimen containers (not shown) to the device 10 for rotation relative to the base unit 12 in a horizontal circular path about the central vertical axis of rotation "A". Thus, in use, the specimen containers are safely secured to the carrousel 14 and are rotated relative to the light source 16 into positions in which at least selected ones of the specimen containers are illuminated from below by the light source 16.

Preferably, the carrousel 14 permits numerous specimen containers to be secured to the device 10 but permits only one specimen container at a time to be illuminated by the light source 16. This arrangement properly focuses the attention of the physician, nurse, and/or technician to the selected illuminated specimen container and thereby reduces the potential for error. In addition, since the specimen containers are engaged and held by the device 10, the use of the device 10 reduces the potential for mishandling and spillage, frees the hands of a physician, nurse, and/or technician, and permits a physician, nurse, and/or technician to quickly confirm the presence and quality of a specimen.

Turning first to the specific structure of one contemplated embodiment of the base unit 12, preferably it has a sealed water-proof plastic housing 24 which can be readily cleaned and sterilized with, for instance, antibacterial sprays. The housing 24 is supported on non-slip feet 26 to ensure that the base unit 12 remains stationary relative to the carrousel 14 and to the surface on which it is supported. A stainless steel shaft 28 extends upwardly from the base unit 12 and provides a means for rotatably supporting the carrousel 14. The light source 16 and a waterproof on/off switch 30 are mounted within the housing 24 and are connected to an AC or DC power source. Preferably, as illustrated, the power source is a rechargeable DC battery pack 32 mounted within the housing 24.

Figure 2:
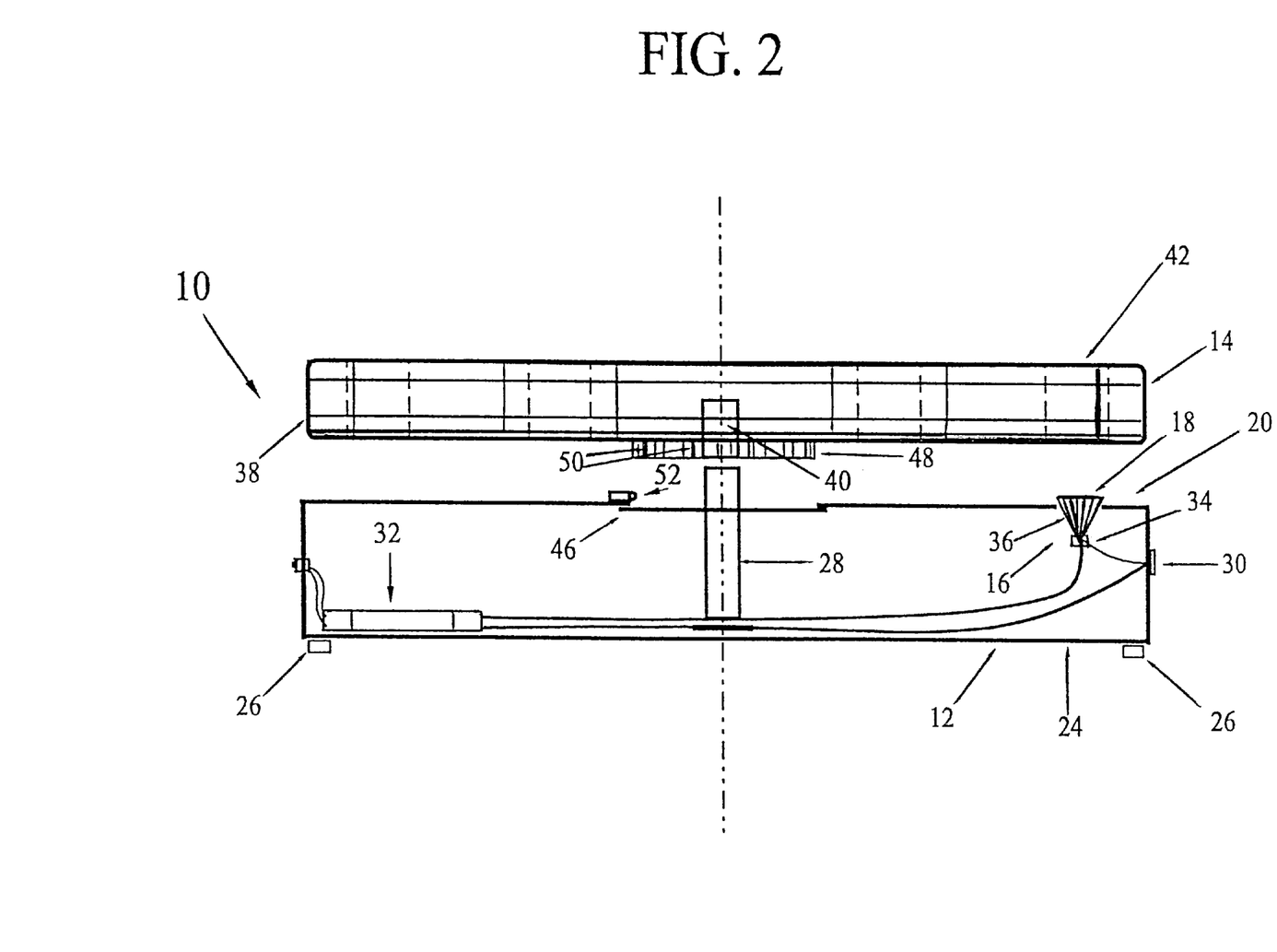
FIG. 2 is am exploded cross-sectional view of the biopsy collection device of FIG. 1 taken along lines 2—2.
Figure 10:
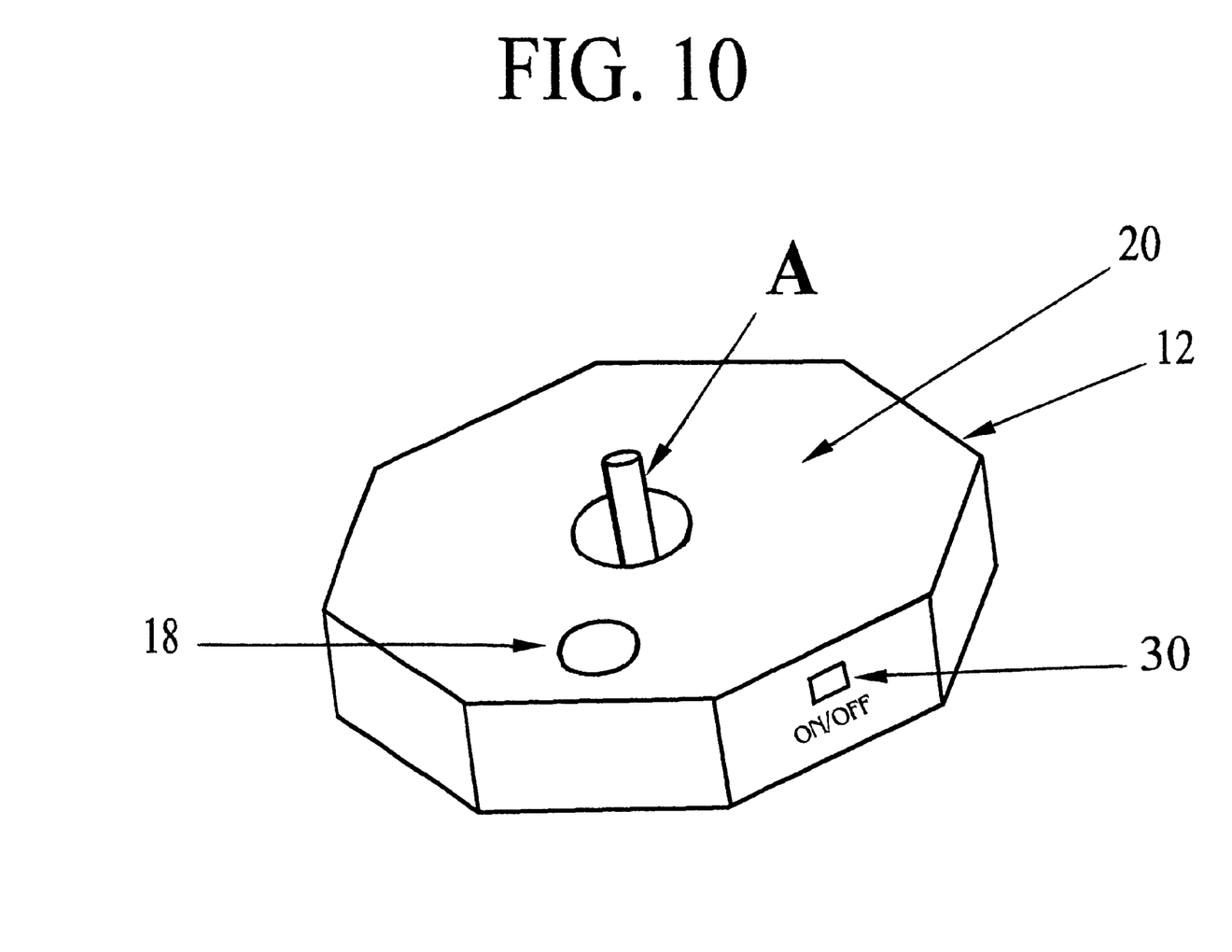
FIG. 10 is a perspective view of one embodiment of a base unit of the biopsy collection device according to the present invention.

The light source 16 is positioned within the housing 24 to emit light through a relatively small window 18 formed in the upper surface 20 of the housing 24 thereby directing light onto a relatively small region of the carrousel 14. As best illustrated in FIGS. 2 and 10, the window 18 is located a spaced distance from the shaft 28 which defines the axis of rotation "A" of the carrousel 14. Thus, the location of the light source 16 is such that it projects light upwardly through a portion of the circular path of rotation of the specimen containers on the carrousel 14 sufficient to light only a selected one of the specimen containers which is located directly over the window 18. Preferably, the light source 16 is provided by a high output LED light 34 mounted within a parabolic reflector 36 which focuses light upwardly through the window 18. The window 18 can be provided with a series of apertures (not shown) to gently diffuse the light emitted outwardly from the base unit 12.

Turning to the specific structure of a contemplated embodiment of the carrousel 14, preferably it has an underside 38 with a bearing assembly 40 which removably seats on the shaft 28 projecting from the base unit 12 so that the carrousel 14 is freely rotatable on the base unit 12. In addition, preferably the carrousel 14 has an upper surface 42 sufficiently spaced from its underside 38 to permit the formation of recesses 44 utilized to hold specimen containers. The recesses 44 open upwardly and are spaced from each other and from the vertical central axis of rotation "A". Thus, each recess 44 can hold a single specimen container and transport the specimen container in a circular horizontal path of rotation about axis "A". Thus, by rotating the carrousel 14 on the base unit 12, a selected one of the specimen containers is located above the light source 16 and is illuminated for specimen visualization purposes.

Preferably, the recesses 44 are equally spaced from axis "A" such that all specimen containers are rotated along the same circular path.

As best illustrated in FIG. 2, preferably a positive stop mechanism 46 is formed at the junction of the carrousel 14 and the base unit 12. To this end, the bearing assembly 40 has an outer annular surface 48 on which grooves 50 are formed corresponding to the location of the recesses 44 on the carrousel 14. A resiliently mounted stop 52 extends from the base unit 12 for engaging the outer annular surface 48 of the bearing assembly 40. Thus, as the carrousel 14 is rotated, the resilient stop 52 projects into the grooves 50 to stop the carrousel 14 at precise locations to accurately align the recesses 44 with the light emanating from the base unit 12.

Figure 6:
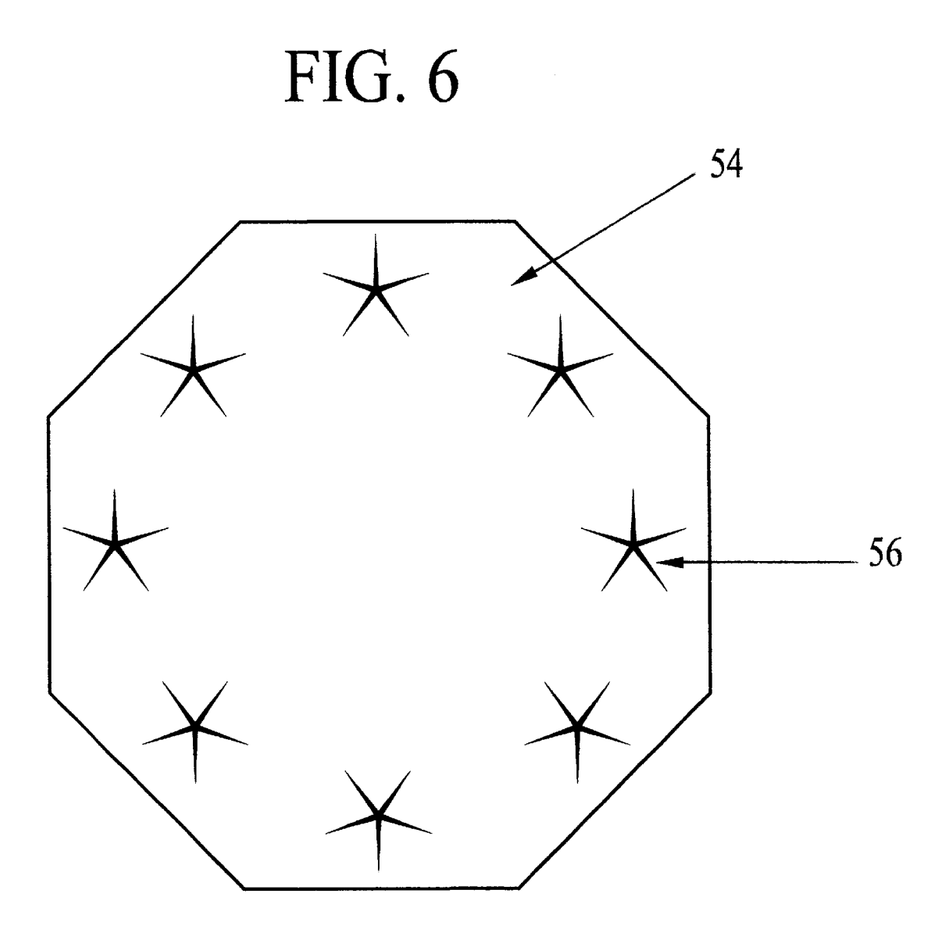
FIG. 6 is a plan view of the gasket layer of the carrousel illustrated in FIG. 3.

Preferably, each recess 44 has means for positively engaging and holding a specimen container to the carrousel 14. To this end, a resilient deformable gasket 54, such as a rubber gasket, extends within each recess 44 and has a slotted opening 56 such as illustrated in FIG. 6. The slotted opening 56 expands and engages the sidewall of a specimen container and firmly holds the specimen container in place on the device 10. In addition, the resilient nature of the gasket 54 permits it to receive and hold specimen containers regardless of the size of the specimen container so that the device 10 can be utilized with different sized specimen containers.

Figure 7:
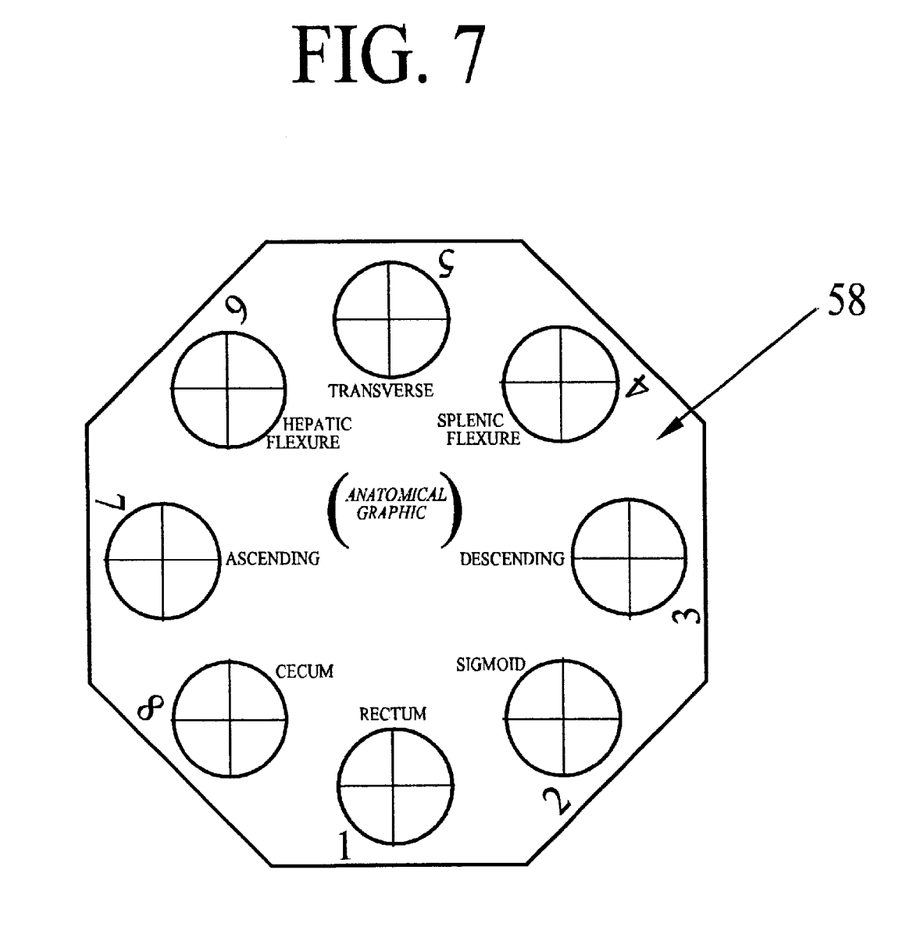
FIG. 7 is a plan view of a graphic overlay for use on the carrousel.

The carrousel 14 of the present invention also provides the function of identifying/labeling the biopsy specimens based on the location of the specimen containers on the carrousel 14. For example, a graphic overlay 58 such as illustrated in FIG. 7 can be utilized on the carrousel 14 so that each recess 44 is defined as containing a particular biopsy. Thus, when the carrousel 14 of the device 10 is removed from the base unit 12 and transported to the pathology department, the pathology department personnel can readily determine the various biopsy specimens obtained by referring to the graphic information adjacent each recess 44 on the carrousel 14. Alternatively, each recess 44 can be marked with a number or some other coded indicia which provides a biopsy identifying function. Thus, the device 10 of the present invention provides an aid for clearly designating various different specimens and thereby reduces the potential for labeling errors.

Figure 3:
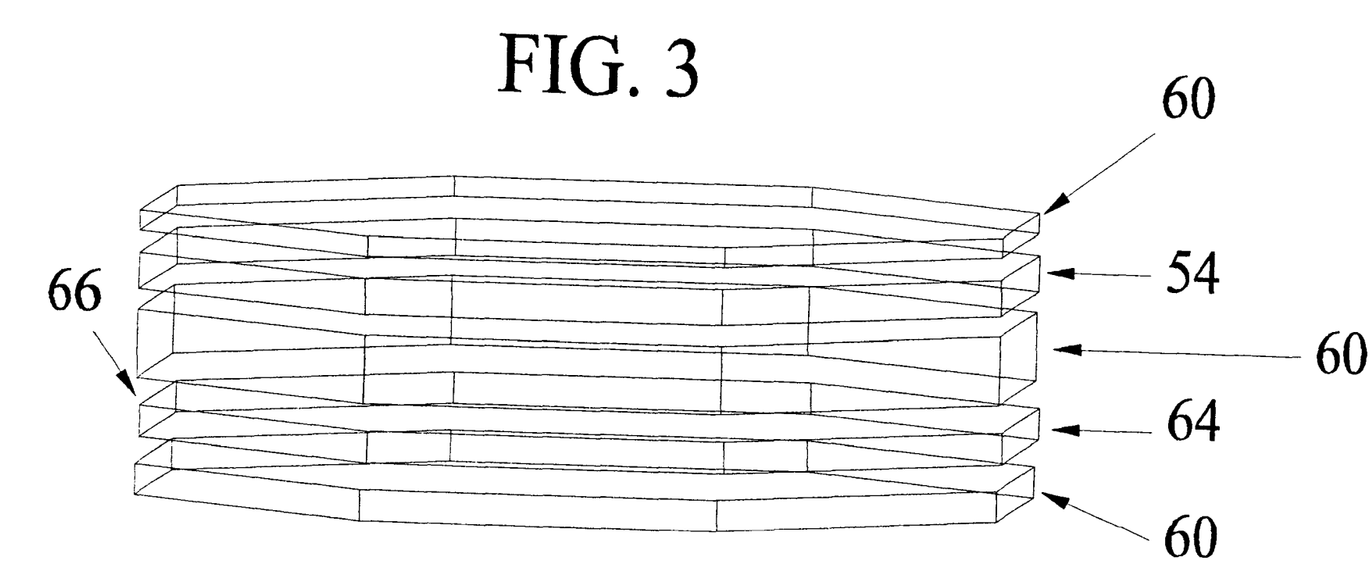
FIG. 3 is an elevational view of one embodiment of a carrousel of the biopsy collection device according to the present invention.
Figure 4:
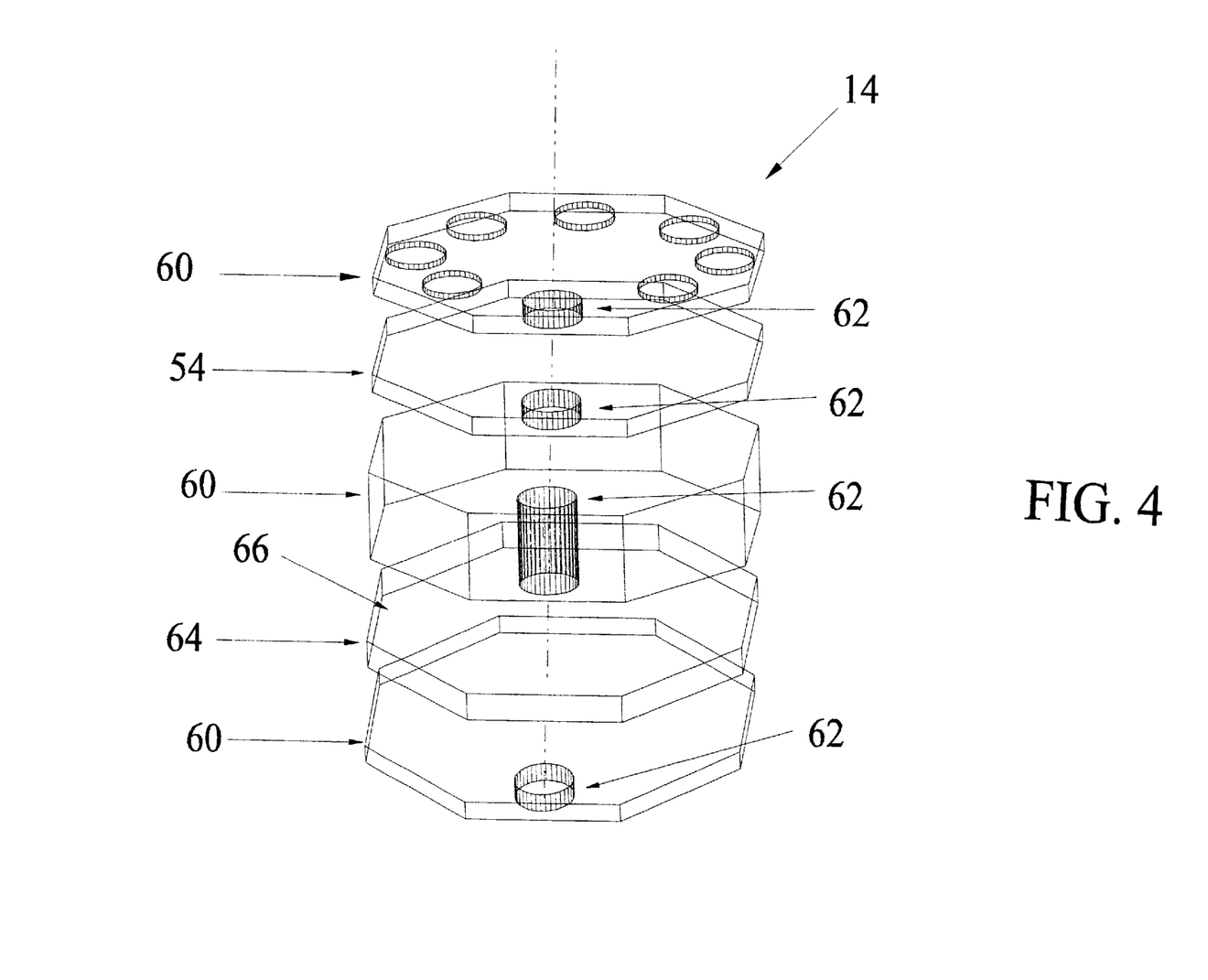
FIG. 4 is an exploded elevational view of the carrousel illustrated in FIG. 3.
Figure 5:
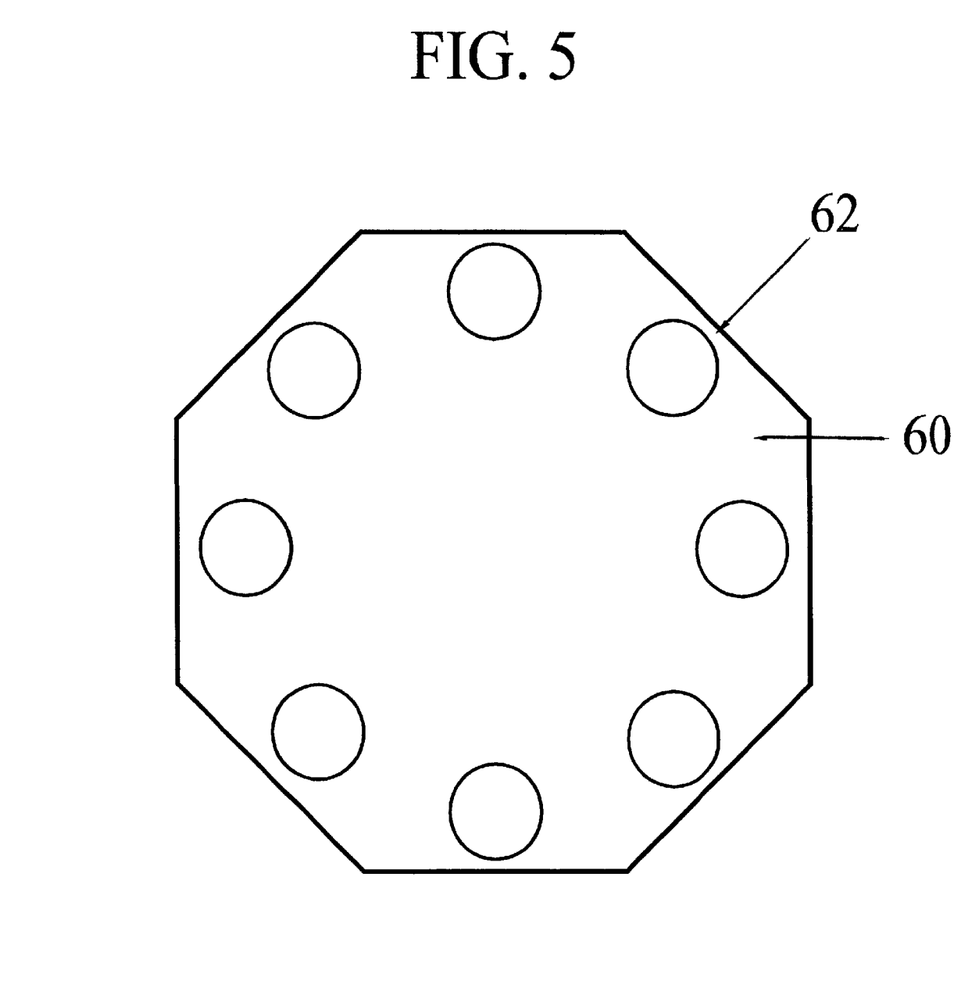
FIG. 5 is a plan view of one of the spacing layers of the carrousel illustrated in FIG. 3.

The carrousel 14 is preferably constructed of multiple horizontally-disposed layers as illustrated in FIGS. 3 and 4. The construction utilizes a plurality of spacing layers 60 which can be made, for instance, of plastic and have aligned apertures 62 which form the recesses 44. The multi-layer carrousel 14 also includes a support layer 64 which forms a the base 66 of each recess 44 and provides a surface on which specimen containers are seated. The support layer 64 permits light shining from the base unit 12 to shine through the bottom 66 of the recess 44 and into the specimen container to aid in visualization of the biopsy specimen. Preferably the support layer 64 is a diffusing lens so that the light is evenly distributed within the specimen container. The multi-layer carrousel 14 also includes a gasket layer 54 as illustrated in FIG. 6 which is spaced from the support layer 64 by at least one spacing layer 60. The slotted openings 56 of the gasket layer 54 extend within the recesses 44 for purposes previously discussed.

Figure 8:
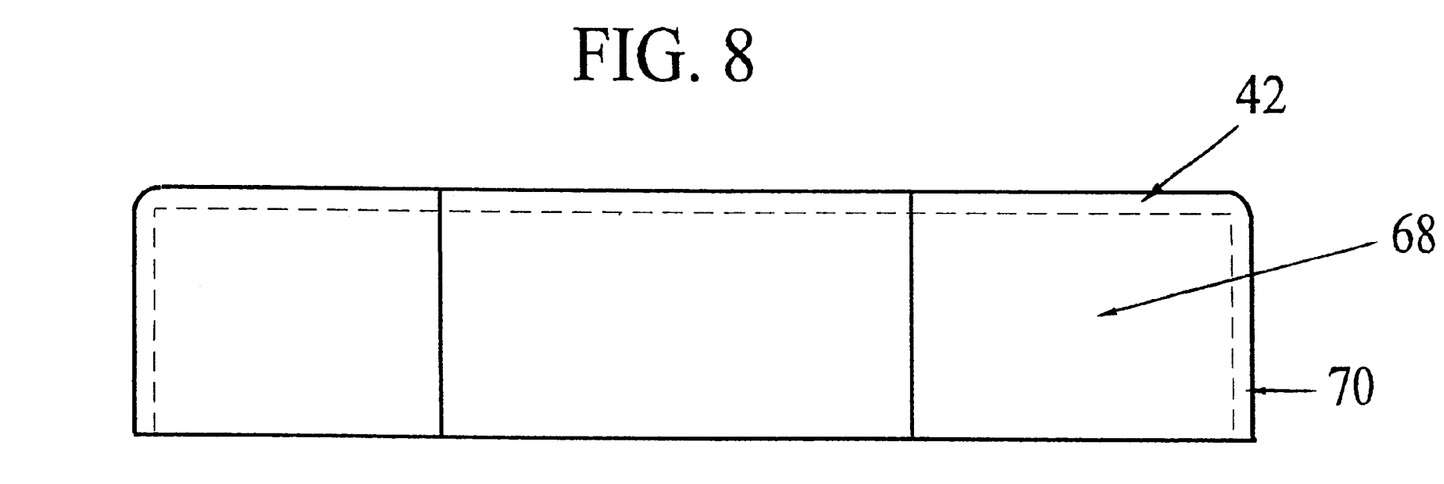
FIG. 8 is a elevational view of an overlay layer of the carrousel.
Figure 9:
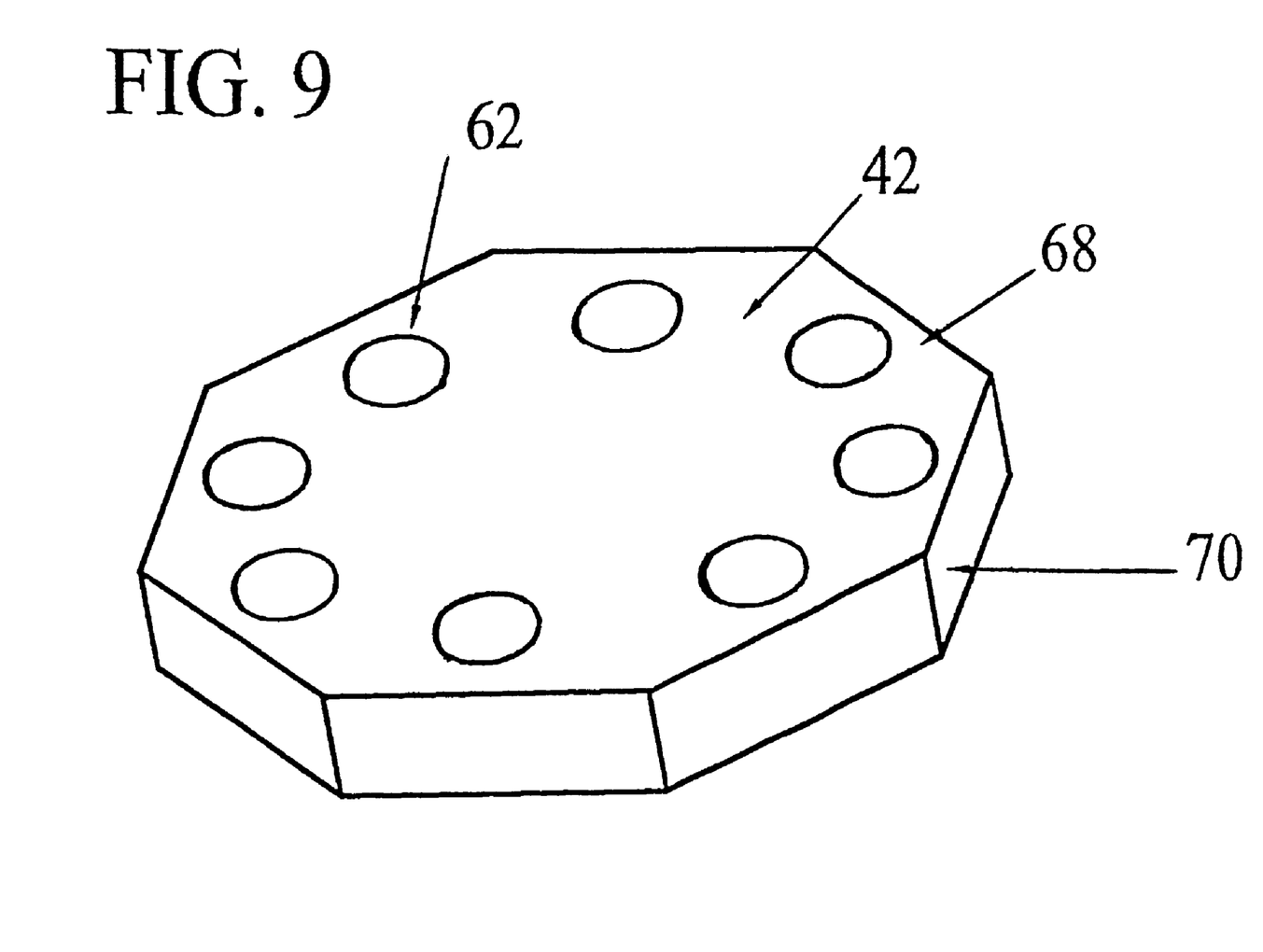
FIG. 9 is a perspective view of the overlay layer illustrated in FIG. 8.

Preferably, as illustrated in FIGS. 8 and 9, the uppermost layer 68 of the multi-layer carrousel 14 is an overlay layer 68 which provides the top and side surfaces, 42 and 70, of the carrousel 14 and seals the other layers, 60, 64 and 54, therein so that the layers are sealed therein and so that the carrousel 14 can be readily washed and sterilized. As stated above, a graphic overlay 58 or other indicia can be secured to, or formed on, the top surface 42 of the overlay layer 68 or underneath a transparent section of the overlay layer 68.

Although a preferred carrousel is illustrated and discussed, other carrousel structures can be utilized. For instance, the carrousel can be formed as a substantially planar piece having upstanding cups or prongs for securing specimen containers thereto. In addition, the device of the present invention can be provided with a stationary carrousel and a rotating base and/or light source. Another alternative includes a base unit housing a plurality of light sources which are controlled to provide the appearance of a rotating light source.

By way of example and not by way of limitation, the device of the present invention can have a base unit which is maintenance free. To this end, a high output LED lighting system can be powered by a 3.6 volt Nickel Cadmium rechargeable battery pack which includes two batteries that interchangeably charge to provide continuous power to the lighting system. The carrousel can have an octagonal shape in plan and provide eight recesses for holding eight specimen containers. The bearing assembly of the carrousel can be made of bronze and can freely slide onto and off the stainless steel shaft projecting from the base unit. The device can be lightweight, portable and made substantially of plastic.

Turning to the method of the present invention, biopsy specimens are taken and placed in transparent specimen containers during a biopsy collection procedure. The specimen containers are secured within designated recesses 44, or other holding means 22, provided on the biopsy collection device 10. Preferably, each recess 44 is designated for a specific type of biopsy, for instance, with respect to the location within the body of where the biopsy specimen was taken. See FIG. 7. Thus, the method includes the step of positively identifying/labeling each specimen by locating the specimen container on the carrousel 14 in a specifically designated recess 44.

Upon placing the specimen container and specimen on the carrousel 14, the carrousel 14 can be rotated so that light is directed from below through the specimen container so that the specimen can be visualized. If a desired specimen cannot be visualized, or if the quality of the specimen is insufficient, another specimen can be promptly taken during the same procedure without delay. The ability to accurate and quickly visualize the specimen eliminates unduly lengthening the biopsy collection procedure and the potential requirement of having to repeat the procedure at a later date. Preferably, the device 10 illuminates the specimen containers one at a time to prevent distraction and error.

Thus, the above described device and method provide significant advantages over current biopsy collection procedures. The present invention reduces the potential of spillage and mishandling since the specimen containers are firmly engaged and secured to the device. In addition, the specimens can be quickly visualized to confirm the presence or lack thereof of specimens of adequate quality. This eliminates delays and the need to repeat biopsy collection procedures. Furthermore, the types of the specimens are clearly labeled based on the location on which they are secured to the device relative to graphic information displayed adjacent each recess. Thus, information concerning the identity of each specimen is readily communicated during the collection procedure and to the pathology department.

While a preferred embodiment of a biopsy collection device and method of collecting biopsy specimens have been described, various modifications, alterations, and changes may be made without departing from the spirit and scope of the present invention as defined in the appended claims.

What is claimed is:

1. A biopsy collection device for use in safely securing and positively visualizing a biopsy specimen located in a specimen container, comprising:

a base unit housing a light source directing light upwardly through said base unit; and a carrousel mounted on said base unit and rotatable relative to said base unit, said carrousel having a plurality of securement means each for positively and safely securing a specimen container to said carrousel such that rotation of said carrousel relative to said base unit positions at least a selected one of said securement means in a position for illumination by said light source thereby aiding the visualization of a biopsy specimen located in the specimen container secured by said securement means;

said plurality of specimen container securement means being a plurality of spaced-apart, upwardly-opening recesses formed in the carrousel, each recess for use in positively holding a single specimen container; and said carrousel having a multi-layer construction including a horizontally-disposed light diffusing layer, a horizontally disposed rubber gasket layer spaced above said light diffusing layer by at least one horizontally disposed spacing layer having apertures defining said plurality of recesses of said carrousel, and at least one overlay layer forming an upper surface of said carrousel and having apertures which are vertically aligned with said apertures of said spacing layer, said rubber gasket layer having slotted openings within each recess.

2. A biopsy collection device according to claim 1, wherein said carrousel includes a graphic overlay which positively identifies each recess with a corresponding predetermined biopsy specimen type.

3. A biopsy collection device according to claim 1, wherein said carrousel rotates about a vertical axis of rotation which extends centrally through said carrousel, and wherein said recesses extend parallel to said axis of rotation and are spaced from said axis of rotation such that each recess rotates in the same horizontal circular path about said axis of rotation.

4. A biopsy collection device according to claim 3, wherein a resilient deformable gasket having a slotted opening extends within at least one of said recesses to enable different sized specimen containers to be positively and safely secured within said recess.

5. A biopsy collection device according to claim 3, wherein said base unit has a window through which light from said light source is directed, said window being located directly beneath a portion of said path of rotation of said recesses so that light from said light source is directly through only one recess at any given time.

6. A biopsy collection device according to claim 5, further comprising a positive stop mechanism for accurately aligning each of said recesses directly above said window of said base unit when said carrousel is rotated on said base unit and one of said recesses passes over said window.

7. A biopsy collection device according to claim 5, wherein said light source comprises high output LED lights and a parabolic reflector which focuses light upwardly through said window formed in said base unit.

8. A biopsy collection device according to claim 5, wherein each recess in said carrousel has a base formed by a horizontal support surface which permits light to pass therethrough into said recess, and wherein at least one of said window on said base unit and said support surfaces of said carrousel is a light diffusing lens.

9. A biopsy collection device according to claim 1, wherein said base unit includes a vertically disposed shaft on which said carrousel is seated and rotates.

10. A biopsy collection device according to claim 9, wherein said base unit is portable, has non-slip feet for maintaining said base unit in a stationary position as said carousel is rotated and houses a rechargeable battery for energizing said light source and an on/off switch for activating said light source.

11. A biopsy collection device for use in safely securing and positively visualizing a biopsy specimen located in a specimen container, comprising:

a base unit housing a light source directing light upwardly through a window formed in said base unit, said light source including a high output LED light and a parabolic reflector for focusing light emitted by said high output LED light upwardly through said window; and a carrousel rotatably mounted on said base unit and having a plurality of spaced-apart, upwardly-opening recesses for positively and safely securing specimen containers on said carrousel for rotation therewith in a horizontal circular path of rotation above said base unit;

said window of said base unit being located directly beneath a portion of said circular path of rotation of said recesses so that light from said light source is directly through only one recess at any given time;

each of said recesses having a resilient deformable gasket with a slotted opening for engaging and securing a specimen container in each of said recesses and enables different sized specimen containers to be positively and safely secured within each of said recesses; and said carrousel having a multi-layer construction including a horizontally-disposed light diffusing layer, a horizontally disposed rubber gasket layer spaced above said light diffusing layer by at least one horizontally disposed spacing layer having apertures defining said plurality of recesses of said carrousel, and at least one overlay layer forming an upper surface of said carrousel and having apertures which are vertically aligned with said apertures of said spacing layer, said rubber gasket layer forming said resilient deformable gasket within each recess;

whereby the light from said light source aids in the ready visualization of biopsy specimens located in specimen containers secured on said carrousel.

12. A biopsy collection device according to claim 11, wherein said carrousel includes a graphic indicia which positively identifies each recess with a corresponding predetermined biopsy specimen.

13. A biopsy collection device according to claim 12, further comprising a positive stop mechanism for accurately aligning each of said recesses directly above said window of said base unit when said carrousel is rotated on said base unit and one of said recesses passes over said window.

14. A biopsy collection device according to claim 13, wherein each recess in said carrousel has a base formed by a horizontal support surface which permits light to pass therethrough into said recess, and wherein at least one of said window on said base unit and said support surfaces of said carrousel is a light diffusing lens.

* * * * *